US008790658B2

(12) United States Patent
Cigarini et al.

(10) Patent No.: US 8,790,658 B2
(45) Date of Patent: Jul. 29, 2014

(54) ANTIGEN-ADJUVANT COMPOSITIONS AND METHODS

(75) Inventors: Sandrine Cigarini, Saint Genis les Ollieres (FR); Kevin Harper, Cheltenham (CA); Manvi Hasija, Mississauga (CA)

(73) Assignee: Sanofi Pasteur Limited, Toronto, Ontario (CA)

( * ) Notice: Subject to any disclaimer, the term of this patent is extended or adjusted under 35 U.S.C. 154(b) by 0 days.

(21) Appl. No.: 12/179,861

(22) Filed: Jul. 25, 2008

(65) Prior Publication Data

US 2009/0110699 A1 Apr. 30, 2009

Related U.S. Application Data

(60) Provisional application No. 60/952,225, filed on Jul. 26, 2007.

(51) Int. Cl.
*A61K 39/00* (2006.01)
*A61K 39/05* (2006.01)
*A61K 39/108* (2006.01)

(52) U.S. Cl.
USPC .................. 424/226.1; 424/184.1; 424/227.1; 424/244.1

(58) Field of Classification Search
None
See application file for complete search history.

(56) References Cited

U.S. PATENT DOCUMENTS

| | | | | |
|---|---|---|---|---|
| 5,766,520 | A | 6/1998 | Bronshtein | |
| 6,509,146 | B1 | 1/2003 | Bronshtein | |
| 6,872,357 | B1 | 3/2005 | Bronshtein | |
| 6,893,657 | B2 | 5/2005 | Roser et al. | |
| 6,964,771 | B1 * | 11/2005 | Roser et al. | 424/400 |
| 2003/0022333 | A1 | 1/2003 | Bronshtein | |
| 2005/0191310 | A1 * | 9/2005 | Kensil et al. | 424/185.1 |
| 2006/0127414 | A1 | 6/2006 | Mayeresse et al. | |
| 2006/0127415 | A1 | 6/2006 | Mayeresse | |

FOREIGN PATENT DOCUMENTS

| | | | |
|---|---|---|---|
| CA | 2312233 | A1 | 6/1999 |
| CA | 2365277 | A1 | 11/2000 |
| CA | 2564674 | B1 | 11/2005 |
| WO | WO9640077 | A2 | 12/1996 |
| WO | WO2005117962 | A1 | 12/2005 |

OTHER PUBLICATIONS

Chang, Degree of antigen absorption in the vaccine or interstitial fluid and its effect on the antibody response in rabbits, Vaccine Apr. 19, 2001 2884-2889.
Bronshtein, Preservation by Foam Formulation, Pharmaceutical Technology (2004) 86-92.
Shi, Change in the degree of absorption of proteins by aluminum-containing adjuvants following exposure to interstitial fluid: freshly prepared and aged model vaccines, Vaccine 20 (2002) 80-85.
Heimlich, The in vitro displacement of absorbed model antigens from aluminium-containing adjuvants by interstitial proteins, Vaccine 17 (1999) 2873-2881.
Seeber, Pedicting the absorporion of proteins by aluminium-containing adjuvants, Vaccine 9 (1991) 201-203.
Hem, Structure and Properties of Aluminum-Containing Adjuvants, Pharm. Biotech vol. 6, Vaccine Design: The Subunit and Adjuvant Approach (1995) 249-276.

* cited by examiner

*Primary Examiner* — Agnieszka Boesen
(74) *Attorney, Agent, or Firm* — Patrick J. Halloran; Reza Yacoob

(57) ABSTRACT

Vitreous compositions of an antigen and adjuvant, and methods for making the compositions are disclosed. Also disclosed are pharmaceutically acceptable formulations of the vitreous compositions, reconstituted liquid formulations of the vitreous compositions, vaccine compositions, and kits containing the vitreous compositions. Also disclosed are devices for administering the vitreous compositions to mammals and methods for eliciting an immune response in mammals by administering the compositions.

8 Claims, 11 Drawing Sheets

C B A

C B A

F1 F2 F3 F4 F5 F6

ANTIGEN-ADJUVANT COMPOSITIONS AND METHODS

CROSS REFERENCE TO RELATED APPLICATIONS

This application claims priority to provisional application No. 60/952,225, filed Jul. 26, 2007, which is incorporated herein by reference.

BACKGROUND

Vaccine compositions generally include one or more antigens, but may also include one or more adjuvants, as well as various other components. Although vaccine compositions are frequently administered to individuals in liquid form, dried vaccine compositions are often preferred for storage and transportation purposes. Stability over time of the components of dried vaccine compositions may be enhanced relative to liquid compositions and the dried compositions may not require refrigeration. Dried compositions can then be reconstituted into a liquid formulation before administration to an individual. Methods for preparing dried vaccine compositions, however, can affect the immunogenicity of the compositions, possibly by altering the integrity of components that make up the compositions. For example, lyophilization or freeze drying of compositions containing aluminum salt adjuvants (e.g., aluminum phosphate adjuvant, aluminum hydroxide adjuvant, alum) may result in loss of immunogenic activity.

In addition to the overall integrity of its individual components, the interactions between certain components within a vaccine composition can also affect immunogenicity of the composition. In one example, adsorption of antigens to aluminum salt adjuvants is believed to enhance immunogenicity of the antigens within a vaccine composition. A variety of factors may affect the ability of antigens to adsorb to the adjuvants in vaccine compositions, including for example, electronic charge of both antigen and adjuvant, pH, temperature, ionic strength, presence of excipients, and other factors. Methods for preparing vaccine compositions, including methods for preparing dried compositions, will also generally affect the association between antigen and adjuvant.

An inability to obtain stable and immunogenic dried vaccine preparations containing antigens and mineral salt adjuvants (e.g. aluminum salts) can affect worldwide distribution of vaccines, particularly to developing countries. Without dried preparations containing both antigen and adjuvant, less stable and more temperature sensitive liquid preparations generally are used. In one example of this, liquid preparations of aluminum salt adjuvants are generally used to reconstitute dried antigen components. Variances in this reconstitution procedure can affect the efficacy of the vaccine product, particularly in areas where there is a lack of skilled medical personnel. The World Health Organization (WHO) has identified this as a major area of concern. In contrast, reconstitution of a single dried preparation containing both antigen and aluminum salt adjuvant is relatively straightforward.

SUMMARY

Vitreous compositions of antigens and adjuvants are disclosed. In one example, the vitreous compositions are in the form of a foam. In one example, the antigens are proteins or peptides. In one example, the adjuvants are aluminum salt adjuvants. In one example, the vitreous compositions contain polyols and/or synthetic polymers that can form a glass. Pharmaceutically acceptable formulations, as well as reconstituted liquid formulations of the vitreous compositions are also disclosed. Methods for preparing the vitreous compositions, as well as for administering and eliciting immune responses in mammals, are disclosed. Kits containing the vitreous compositions and microneedle arrays coated with the vitreous compositions are also disclosed.

BRIEF DESCRIPTION OF THE DRAWINGS

In the accompanying drawings, which are incorporated in and constitute a part of the specification, embodiments of vaccine compositions and methods of producing vaccine compositions are illustrated which, together with the detailed description given below, serve to describe the examples. It will be appreciated that the embodiments illustrated in the drawings are shown for the purpose of illustration and not for limitation. It will be appreciated that changes, modifications and deviations from the embodiments illustrated in the drawings may be made without departing from the spirit and scope of the invention, as disclosed below.

DETAILED DESCRIPTION

Figure 1:
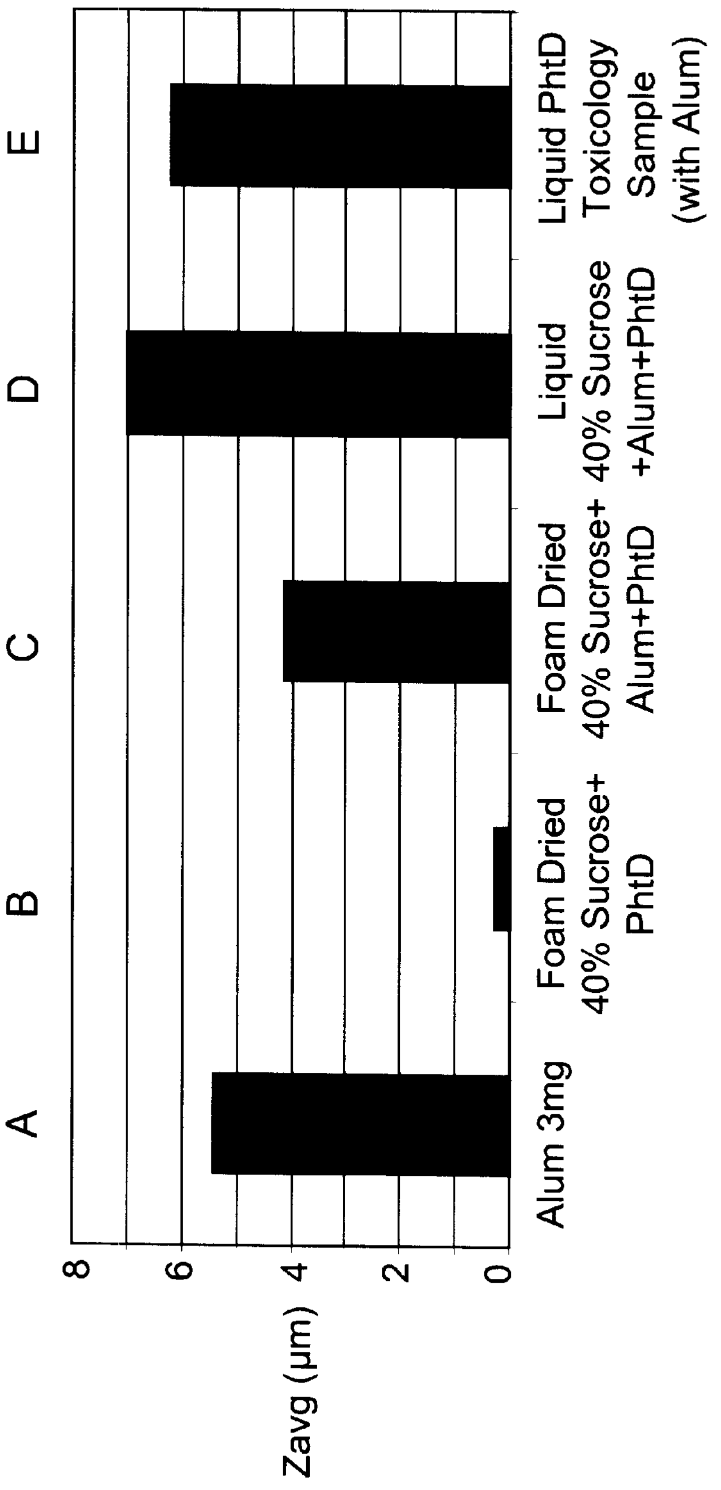
FIG. 1 illustrates example results of a study examining the effects of foam drying on aluminum adjuvant stability in various preparations as described in more detail in Example 2 herein. The vertical axis is a measure of mean particle size in microns.

This application describes solid vitreous compositions of antigens and adjuvants. In one example, the vitreous compositions are in the form of mechanically stable porous structures or foams. In one example, the antigens within the vitreous compositions are adsorbed to the adjuvants. Methods for making the vitreous compositions are disclosed. In the instance where the vitreous composition is a foam, a method for making the composition is disclosed and is called foam drying. Also disclosed are pharmaceutically acceptable formulations of the vitreous compositions and methods for preparing these compositions. Reconstituted liquid forms of a solid vitreous composition of an antigen and adjuvant are disclosed. Also disclosed are methods for eliciting an immune response in a mammal using formulations of the vitreous antigen and adjuvant compositions, kits containing the vitreous compositions, and methods and devices for use in administering formulations of the vitreous compositions to mammals.

Definitions

The following includes definitions of selected terms that may be used throughout the disclosure. The definitions include various examples and/or forms of components that fall within the scope of a term and that may be used for implementation. The examples are not intended to be limiting. Both singular and plural forms of the terms fall within the definitions.

"Adjuvant", as used herein, refers to agents or substances that modulate the immunogenicity of an antigen. "Modulate the immunogenicity" includes enhancing the magnitude, duration and/or specificity of an immune response stimulated by an antigen.

"Amorphous solid", as used herein, refers to solids substantially lacking crystalline structure.

"Antigen", as used herein, refers to a substance capable of initiating and mediating an immune response. Antigens that stimulate or potentiate immune responses are said to be immunogenic and may be referred to as immunogens.

"Boiling", as used herein, refers to a phase transition that occurs when a liquid is vaporized. The "boiling point", is a property of a liquid at a given pressure and is defined as the temperature at which the vapor pressure of the liquid is equal to the external pressure to which the liquid is exposed. Boiling is generally visually observed as bubbling within the liquid.

"Foam", as used herein, refers to a type of amorphous solid that has a mechanically stable porous structure. A foam may also be referred to as a "foamed glass."

"Foam drying", as used herein, refers to a process of forming a foam. Foam drying is a type of vitrification process.

"Glass", as used herein, refers to a type of substantially non-porous amorphous solid.

"Glass transition temperature", as used herein, refers to the temperature at which a vitreous solid is formed. Amorphous solids are in a glassy state below the glass transition temperature. The glass transition temperature may be abbreviated as "$T_g$".

"Polyol", as used herein, refers to polyalcohols, and more generally may refer to substances capable of forming glasses and/or foams.

"Vaccine", as used herein, refers to a pharmaceutically acceptable formulation of at least one antigen. Such pharmaceutical acceptable formulations of an antigen may also include adjuvants, excipients, diluents, etc. that enhance the activity, stability, etc. of a formulation or administration.

"Vacuum", as used herein, refers to a pressure less than 1 atm or 760 Torr.

"Viscous", as used herein, refers to the "thickness" of a liquid or its internal resistance to flow. Herein, a liquid that is referred to as viscous generally is a fluid that can be boiled under a vacuum, as is performed in the foam drying process as disclosed below. Viscous liquids may also be referred to as syrups. Herein, viscous liquids generally have a viscosity in the range of $10^6$-$10^7$ Pascal seconds.

"Vitreous composition", as used herein, refers to a type of amorphous solid that includes foams and glasses.

"Vitrification", as used herein, refers to a process for converting a material into a vitreous composition.

Antigens

Antigens are generally substances capable of stimulating immune responses (i.e., antigens are potentially immunogenic). The immune responses stimulated by antigens may be one or both of humoral or cellular, and generally are specific for the antigen. Antigens, therefore, are substances that may be bound by antibody molecules or by T cell receptors. Many types of biological and other molecules can act as antigens. For example, antigens may originate from molecules that include, but are not limited to, proteins, peptides, carbohydrates, polysaccharides, oligosaccharides, sugars, lipids, phospholipids, metabolites, hormones, nucleic acids, and other molecules, and fragments and/or combinations thereof. Antigens of any of these origins and types, as well as others not listed, may be used in the vitreous compositions and processes described herein.

Antigens may originate from innate sources (e.g., self antigens, autoantigens, tumor-associated antigens) or from sources extrinsic to a particular mammal or other animal (e.g., from infectious agents). Antigens may possess multiple antigenic determinants such that exposure of a mammal to an antigen may produce a plurality of corresponding antibodies or cellular immune responses with differing specificities. Antigens may be purposefully introduced into a mammal for purposes of eliciting an immune response (e.g., immunization) by a variety of routes, including but not limited to, ingestion, inhalation, skin contact, subcutaneous injection, intravenous injection, intramuscular injection, intradermal injection, contact with mucosal surfaces and by other routes.

Antigens may include or be part of components larger than single molecules, such as all or parts of cells, bacteria, viruses, and other microorganisms, and part or combinations of these. Bacteria and viruses, particularly those responsible for diseases in mammals, are sources of antigens that may be useful in the vitreous compositions and processes described herein. Bacterial antigens include proteins, polysaccharides and other molecules derived from the outer surfaces of the cell, from the cell interior, from the flagella, or from other components. Other antigens may be those secreted by an infected cell or released upon cell death or disruption. Examples of these antigens may include diphtheria, tetanus, and botulism toxins.

Examples of antigens which may be used in the vitreous compositions described herein may include, but are not limited to, antigens from rotavirus, the agent for foot and mouth disease, influenza, parainfluenza, herpesvirus species (herpes simplex virus, Epstein Barr virus, chickenpox virus, pseudorabies, cytomegalovirus), rabies virus, polio virus, Hepatitis A, B, C and E, distemper, Venezuelan equine encephalomyelitis, feline leukemia virus, reovirus, respiratory syncytial virus, Lassa fever virus, polyoma virus, canine parvovirus, papilloma virus, tick borne encephalitis, Rinderpest, rhinoviruses, enteroviruses, Mengo virus, paramyxoviruses (mumps, measles, respiratory syncytial virus), avian infectious bronchitis virus, HTLV 1, HIV-1 and -2, influenza virus A, B and C, lymphocytic choriomeningitis virus, parvovirus, adenovirus, togavirus (rubella, yellow fever, dengue fever (e.g., pre-membrane and envelope proteins)), bovine respiratory syncytial virus, coronavirus, Japanese Encephalitis virus, polio virus, *Bordetella pertussis, Brucella abortis, Escherichia coli, Salmonella* species, *Salmonella typhi, Streptococci, Vibrio* (*V. cholera, V. parahaemolyticus*), *Shigella, Pseudomonas, Brucella* species, *Klebsiella*, Mycobacteria species (tuberculosis, *avium*, BCG, leprosy), Pneumococci, Staphylococci, *Enterobacter* species, tetanus, anthrax, *Streptococcus pneumoniae*, meningococcus A, B, C, Y, W, W-135, *Helicobacter pylori, Rochalimaea henselae, Pasteurella* (*P. haemolytica, P. multocida*), *Chlamydia* (*C. trachomatis, C. psittaci*), syphilis (*Treponema pallidum*), *Haemophilus* species, *Haemophilus influenzae* type b, mycoplasma species, Lyme disease (*Borrelia burgdorferi*), Legionnaires' disease, botulism (*Clostridium botulinum*), *Corynebacterium diptheriae, Yersinia entercolitica*, rickettsial infections, Rocky Mountain Spotted Fever, Typhus, Ehrlichia, parasites and protozoa including malaria (*Plasmodium falciparum, P. vivax, P. malariae*), schistosomes, trypanosomes, leishmania, filarial nematodes, trichomoniasis, sarcosporidiasis, *Tacnia* (*T. saginata, T. solium*), *Toxoplasma gondi*, Trichinosis (*Trichinella spiralis*), Coccidiosis (*Eimeria* species), fungi including *Cryptococcus neoformans, Candida albicans, Aspergillus fumigatus*, Coccidioidomycosis, and others.

The antigens employed in the disclosed vitreous compositions and processes may be the naturally occurring form of the antigen as derived from its natural source. The naturally occurring antigens may also be converted to other forms, including less toxic forms, which may be fragments or may contain other deletions, additions or modifications. These converted forms of antigens generally will retain immunogenicity. Diphtheria and tetanus toxoids are examples of detoxified forms of natural antigens, in this case produced by chemical (e.g., formaldehyde) treatment. Other means for eliminating toxicity of antigens are well known and include enzymatic digestion/fragmentation of protein antigens, denaturation (commonly through heat or chemical treatment), conjugation, chemical modification, and others.

It is common in the field to administer multiple antigens in a single vaccine formulation to induce protection against multiple diseases, infectious agents, types, serotypes, serovars, and others, and the compositions of the present disclosure may similarly include multiple antigens. Particular examples of such antigens which are combined include diphtheria, tetanus, pertussis and other antigens. Antigens may also be associated with a carrier protein that mediates the immunogenicity of the antigens. Examples of such conjugated antigens are well known in the art and commercially available in pharmaceutical formulations as vaccines. All of these example antigens, combination antigens, carrier-associated antigens, and others, may be incorporated into the vitreous compositions and processes described herein.

The concentration of the antigen in the vitreous composition may be of any concentration, but generally is sufficient to stimulate an immune system when administered to an individual or mammal. In one example, the concentration of one or more antigens is 10 μg per ml. In other examples, the concentration of one or more antigens may be 20, 30, 40, 50, 100, 150, 200, 250, 300, 350, 400, 450, 500, 550, 600, 650, 700, 750, 800, 850, 900, 950, or 1000 μg/ml. In other examples, the concentration of antigen may be 2, 3, 4, 5, 6, 7, 8, 9, 10 mg/ml or even more. The concentration of the one or more antigens may also be in a range between any two of the values listed above.

Adjuvants

Adjuvants generally are substances that can enhance the immunogenicity of antigens. Adjuvants often are incorporated into vaccine compositions and function during and after the vaccine composition is administered to an individual or mammal. Adjuvants may play a role in both acquired and innate (e.g., toll-like receptors) immunity and may function in a variety of ways, not all of which are understood.

Many substances, both natural and synthetic, have been shown to function as adjuvants. For example, adjuvants may include, but are not limited to, mineral salts, squalene mixtures, muramyl peptide, saponin derivatives, mycobacterium cell wall preparations, certain emulsions, monophosphoryl lipid A, mycolic acid derivatives, nonionic block copolymer surfactants, Quil A, cholera toxin B subunit, polyphosphazene and derivatives, immunostimulating complexes (ISCOMs), cytokine adjuvants, MF59 adjuvant, lipid adjuvants, mucosal adjuvants, certain bacterial exotoxins and other components, certain oligonucleotides, PLG, and others. These adjuvants may be used in the vitreous compositions and methods described herein.

Among the adjuvants useful in the vitreous compositions disclosed herein are mineral salt adjuvants, especially aluminum and calcium salt adjuvants. Aluminum salt adjuvants include aluminum hydroxide adjuvant (crystalline aluminum oxyhydroxide or AlOOH), aluminum phosphate adjuvant (amorphous aluminum hydroxyphosphate) and alum (potassium aluminum sulfate or $AlK(SO_4)_2$). When the adjuvant employed in the composition is an aluminum salt adjuvant, the compositions generally should not be exposed to extreme temperatures, i.e., below freezing (0° C.) or extreme heat (e.g., 70° C.), at least for long periods of time, as it is well known that exposure to extreme temperatures may affect both immunogenic activity of the aluminum adjuvant as well as the adsorbed antigen.

It is known in the art that antigens can adsorb to aluminum salt adjuvants. Electrostatic attraction, at least in part, may be responsible for adsorption of antigens to these adjuvants. The electrostatic interactions between antigen and adjuvant may be optimized by considering the isoelectric point (IEP) of antigens and surface charge (point of zero charge or PZC) of aluminum salt adjuvants. In one example, the IEP of a protein antigen is determined and an aluminum salt adjuvant with an opposite surface charge at the desired pH is selected. For example, at approximately neutral pH, a protein antigen with an IEP<7 will better adsorb to aluminum hydroxide adjuvant (PZC>7) than to aluminum phosphate adjuvant (PZC<7). In contrast, at neutral pH, a protein antigen with an IEP>7 will better adsorb to aluminum phosphate adjuvant than to aluminum hydroxide adjuvant.

As is disclosed herein, the foam drying procedures may partially overcome less than optimum electrostatic interactions between antigens and adjuvant to increase antigen adsorption to adjuvant. This is indicated by increased adsorption of antigen to aluminum salt adjuvants in foam dried preparations of antigen and adjuvant, as compared to adsorption of antigen to aluminum salt adjuvants in preparations that have not been foam dried. These studies and results are described more fully in the Examples of this disclosure. Therefore, the foam drying method can provide a means for using non-optimum combinations of antigen and adjuvant and may provide for novel antigen and adjuvant combinations. In one example, the foam drying method may provide for a composition of a protein antigen with an IEP<7 that is adsorbed to aluminum phosphate adjuvant. In one example, the foam drying method may provide for a composition of a protein antigen with an IEP>7 that is adsorbed to aluminum hydroxide adjuvant. Other compositions of antigen and adjuvant may also be produced. In one example, a composition of a protein antigen with an IEP<7 that is adsorbed to aluminum hydroxide adjuvant is produced. In one example, a composition of a protein antigen with an IEP>7 that is adsorbed to aluminum phosphate adjuvant is produced.

The concentration of the adjuvant in the vitreous composition may be of any concentration, but generally is sufficient to enhance an antigen's ability to stimulate the immune system when administered to an individual or mammal. In one example, the concentration of one or more adjuvants is 0.1 mg/ml. In other examples, the concentration of the one or more adjuvants is 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or even 10.0 mg/ml or even more. The concentration of the one or more adjuvants may also be in a range between any two of the values listed above.

Glass and Foam-Forming Substances

A composition that is to undergo a vitrification process, like foam drying, generally will contain one or more substances capable of forming a vitreous composition, or facilitating formation of a vitreous composition, like a foamed glass. Generally, a liquid formulation containing these substances can be cooled to form a solid substantially free of crystalline structure, like a glass or foam. Generally the conversion or transition from liquid to glass or foam occurs at or near the glass transition temperature ($T_g$). Generally, these substances do not interfere with the activity of antigens or adjuvants within the vitreous compositions. These substances may also stabilize antigens and/or adjuvants and generally do not negatively affect the activity of biological components. These substances also may enhance or facilitate the ability of antigens and/or adjuvants to withstand the drying process and subsequent storage.

A variety of substances capable of forming a glass or foam, or facilitating formation of a glass or foam, can be used. Some of these substances include sugars, carbohydrates, polyols, polymers, proteins, peptides, amino acids (e.g., glycine, alanine, arginine, lysine, glutamine) and others. Combinations of these substances may be used. These substances may be referred to using a variety of names or labels. For example, some of these substances may be referred to as stabilizers, glass- or foam-forming agents, vitrifying enhancers, polyols, protectants, glass or foam matrix-forming materials, as well as other names.

In one example, polyols can be used. Examples of polyols may include simple sugars (e.g., glucose, maltose, sucrose, xylulose, robose, mannose, fructose, raffinose, trehalose and others) or carbohydrate sugars (e.g., mannitol, sorbitol, erythritol, xylitol, maltitol, siomalt, lactitol and others). In some cases, substances like lactose, raffinose, trehalose, sucrose and others, may be referred to as stabilizing sugars. Substances like sorbose, piscose, ribulose, erythrulose and dihydroxydimethylketone may be used. Examples of methylated monosaccharides that may be used may include some arabino, galacto, gluco, manno or xylo pyranosides. In some instances, the term "polyol" may be used to generally refer to substances capable of forming, or facilitating forming, glasses and/or foams.

Monosaccharides, disaccharides, trisaccharides, oligosaccharides and their corresponding sugar alcohols may be used to form or facilitate forming of glasses or foams. Sugar alcohol glycosides may be used. Polyhydroxy compounds, like carbohydrate derivatives and chemically modified carbohydrates may be used. Palatinit (a mixture of α-D-glucopyranosyl-1→6-sorbitol (GPS) and α-D-glucopyranosyl-1→6-mannitol (GPM)) or its individual GPS or GPM components may be used. In some examples, sucrose, methyl α-D-glucoside, 2-HP-β-cyclodextrin and arginine, alone or in various combinations, may be used. Polysaccharides may also be used.

In one example, polymers may also be used in formation, or facilitating or enhancing formation, of the vitreous compositions disclosed herein. Some examples of polymers that may be used include polyethylene glycol, hydroxyethyl starch, polyvinyl pyrrolidone, polyacrylamide, polyethyleneimine, and others. Sugar copolymers, like Ficoll and dextrans, may also be used.

The concentration of the polyol, or other foam- or glass-forming or facilitating substance, or combination of substances, is generally sufficient to achieve a viscous liquid composition, or to achieve a viscous liquid composition after a process step designed to increase the viscosity of the liquid (see discussion of this step below). In one example, the total concentration of polyols, synthetic polymers and other glass- or foam-forming substances is 5%. In one example, the total concentration of polyols, synthetic polymers and other glass- or foam-forming substances is at least 5%. In other examples, the total concentration of these substances is 10%, 15%, 20%, 25%, 30%, 35%, 40%, 45%, 50%, or even higher. The concentration of the one or more glass- or foam-forming substances may also be in a range between any two of the values listed above.

Liquids Containing the Antigen/Adjuvant/Polyol

Generally, a liquid containing the antigens, adjuvants and glass-/foam-forming or facilitating substances (e.g., polyols), and possibly other substances as will be discussed, are combined in a liquid, which is then subjected to the foam drying process as described below. These components can be combined in the liquid in various ways. In one example, the antigens and adjuvants are first combined in a liquid and the polyols are subsequently added. The antigens and adjuvants may be present together in a liquid for a period of time (e.g., 24-48 h) before the polyols are added. The antigen and adjuvant may be incubated at various temperatures (e.g., 2-8° C.) before addition of the polyols. This may facilitate association between the antigen and adjuvant. In another example, the antigens, adjuvants and polyols are added to a liquid concurrently. Other combinations of adding the components are possible.

The liquids containing the antigens, adjuvants and polyols generally are aqueous liquids, although organics may be present in at least some concentration if the organics are compatible with the antigens, adjuvants and polyols that are used. In the case of aqueous liquids, the liquids may be buffered. Generally, the buffering system used is compatible with the antigens, adjuvants and polyols that are used.

Other Substances

Substances other than antigens, adjuvants and polyols may be incorporated into the vitreous compositions. Generally, these other substances would be added to the liquid containing the antigen/adjuvant/polyol that is to be used in the foam drying process. These additional substances may include, for example, substances that aid in solubilizing antigens, adjuvants or polyols that are components of the liquid that is to be foam dried, substances that enhance glass or foam formation or stabilize glasses or foams, substances that affect the $T_g$, substances that enhance drying of the glass or foam, substances that stabilize (e.g., prevent degradation (Maillard reaction) or aggregation) antigens and/or adjuvants in the glass or foam, and substances that perform other functions. Salts may also be added to the liquid to be foam dried and may be incorporated into the vitreous compositions. Other substances, like biologicals, biological modifiers, pharmaceutical agents, and others, may also be added.

Foams and Foam Drying

Vitreous solid forms of antigen/adjuvant/polyol compositions are prepared through vitrification. Vitrification is a process of converting a material into a glass-like amorphous solid which is substantially free from crystalline structure. Vitrification also refers to converting a material into a foam. Solidification of the vitreous solid occurs at the glass transition temperature ($T_g$), which is a property of the material, and occurs during cooling of the material. Glass transition temperature is usually applicable to wholly or partially amorphous phases such as glasses and plastics. At or below the glass transition temperature, the physical properties of amorphous materials are converted to a vitreous amorphous solid.

The vitreous solid forms disclosed herein may be foams. Foams generally are stable porous structures with high surface areas. Foams can be of different thicknesses and generally are less dense than non-foamed forms of similar composition (e.g., true glasses). The foams as disclosed herein have also been termed foamed glasses, foamed glass matrices, dried foams and stabilized foams. Foam drying procedures and equipment to perform the processes and procedures have been disclosed (see e.g., U.S. Pat. Nos. 5,766,520, 6,509,146 and 6,964,771, the entire teachings of which are incorporated by reference). Foam drying processes are generally distinguished from other vitrification protocols by the formation of the foams. Foams can be prepared from a variety of liquids, dispersions, suspensions, emulsions, mixtures and solutions. Generally, at least in the example where the liquids contain antigens, the prepared liquids are compatible with biologicals.

The foam drying process uses boiling of a liquid in a vacuum to cause evaporation of liquid from the sample and formation of the foam. The boiling is performed under a vacuum so that the sample is not subjected to the higher temperatures that would be needed to boil the liquid at atmospheric pressure (i.e., no vacuum present). In one example, the vacuum under which the liquid is boiled is a relatively high vacuum. In one example, the pressure is <25 Torr (less than about 0.033 atm). In other examples, the pressure is <10 Torr (less than about 0.013 atm), <8 Torr (less than about 0.010 atm) or <5 Torr (less than about 0.007 atm). Generally, the vacuum is maintained until a foam is formed, although the vacuum can be maintained for a time after a foam is formed. Continued application of the vacuum may result in decreasing the residual moisture content of the foam that has formed. For example, the vacuum may be maintained for approximately 4 h, but the duration of the vacuum may be more or less than this. In other examples, the vacuum may be maintained for 0.5, 1, 2, 3, 4, 5, 6, 7, 8, 9, 10, 12, 14, 16, 18, 20, 22, 24 or even 48 h.

The evaporation of liquid that occurs during the boiling process generally has a cooling effect on the sample and the sample temperature decreases during boiling. The evaporation of liquid also generally has the effect of increasing the glass transition temperature ($T_g$) of the sample and the sample $T_g$ increases during boiling. At some point in time during the boiling process, the sample temperature and the $T_g$ coincide and are the same. At this point in time, and as the sample temperature continues to decrease below the increasing $T_g$, a vitreous solid is formed. In one example, the vitreous solid is a foam.

During the boiling process, the temperature of the samples may fluctuate, but generally is kept within a range such that desired properties (e.g., immunogenicity) of the biological materials within the samples are retained. In one example, temperatures during the boiling process may be below 100° C. and may be above 0° C. In one example, the temperature of the sample remains below 70° C. and above 0° C. Other temperature ranges are possible. In one example, at least parts of the sample may, at least briefly, go below 0° C. It may be that a slurry is formed. The equipment used to perform this boiling step, to obtain a foam, generally has the ability to control both vacuum and temperature of the samples during the process. In some cases, conventional freeze-drying machines or modified freeze-drying machines may be used.

Prior to the above described "boiling" step of the foam drying process, a process step may be performed that is designed to increase the viscosity of the liquids, dispersions, suspensions, emulsions, mixtures or solutions that are to be subjected boiling step of the foam drying process. In some cases, this step may be optional. This "viscosity-increasing" step can be performed by a variety of methods. In one method, liquid samples can be subjected to a relatively low vacuum (e.g., a pressure in the range of about 0.9 to 0.1 atm). In one example, a pressure of about about 0.2 atm or 152 Torr may be used. Other pressures can be used. For example, the pressure may be <1 atm, <0.9 atm, <0.8 atm, <0.7 atm, <0.6 atm, <0.5 atm, <0.4 atm, <0.3 atm, <0.2 atm, or even <0.1 atm. The relatively low vacuum can be applied at room temperature or at other temperatures. In another method, the liquid may be vaporized by boiling under a vacuum. This step may be separate from or continuous with the boiling step of the foam drying process already described. This latter method can be performed under similar conditions as is the previously described boiling step, although the vacuum and the duration in which the vacuum is applied may be different. At the conclusion of this viscosity-increasing process step, a liquid of higher viscosity than the viscosity of the starting liquid is generally obtained. In some instances, this higher viscosity liquid may be called a syrup. The higher viscosity liquid can be subjected to the boiling step to obtain a foam, as described above.

After the boiling step, there may be a process step included which is designed to dry, or decrease the moisture content of the foam that results from the boiling step. In some cases, this step may be optional. This step can be performed by a variety of methods. In one example, the foam may be subjected to a vacuum (vacuum drying). In one example of vacuum drying, the pressure may be <5 Torr (less than about 0.007 atm). In another example, the pressure may be <1 Torr (less than about 0.0013 atm). Other pressures may be used in the vacuum drying step. In another example, the foam may be stored in the presence of a desicant, such as DRIERITE. In another example, the foam may be vacuum dried in the presence of a desicant. Other methods for decreasing the moisture content of the foam may be used. This "secondary drying" step may be performed at various temperatures and for various durations. For example, the secondary drying may be performed at 25, 37, 40, 55° C., or at other temperatures. For example, the secondary drying may be carried out over a period of hours, days, weeks or months. Often, the secondary drying procedure will proceed for extended periods of time, depending on sample size, initial water concentration, etc. In one example, the procedure is carried out for a period in excess of 12 h and generally more than 24 or 48 h. By routine experimentation, one of skill in the art will be able to identify more precise parameters to achieve sufficient dryness. Alternatively, the concentration of water in the sample may be determined by various sensor systems so that the secondary drying step can be stopped with the desired residual moisture content of the sample is reached.

Generally, at the completion of the secondary drying process step, the residual moisture content of the samples is less than the residual moisture content of the sample before undergoing the secondary drying step. For example, the samples that have completed the secondary drying process may have a residual moisture content of less than 10%, less than 5%, less than 4%, less than 3%, less than 2%, less than 1%, or even lower. Moisture content may be measured using different methods. In one example, the Karl Fisher Technique is used to measure the residual moisture content of the vitreous solid. Decreasing the moisture content of the foam, as is accomplished by this step, is facilitated by an increased surface area of the foam, as compared to vitreous compositions that are not foams.

Further decreasing the moisture content of the sample, as is provided by the above described secondary drying step, is believed to increase the glass transition temperature ($T_g$) of the sample. As described above, the vitreous state is formed during the boiling step as the sample cools below the $T_g$. A subsequent secondary drying step generally causes an additional reduction in moisture content and an increase in $T_g$ of the vitreous sample. Heating or storing a vitreous sample at or above its $T_g$ can cause changes in the vitreous sample that may not be advantageous to long-term stability of the components of the sample. Therefore, the vitreous samples generally are stored below their $T_g$. By reducing moisture content, and thereby raising the $T_g$, the sample may be stored at higher temperatures (and possibly decrease the need for a cold chain or temperature-controlled chain) without affecting stability of the sample or its components. Generally, samples may be cooled to a temperature below the $T_g$ at the conclusion of or after the secondary drying step, in order that the sample remains in a stable form during storage, until the sample is reconstituted as a liquid and administered to an individual.

In one example, that is exemplified herein, the vitreous solid forms of the antigen/adjuvant/polyol compositions are prepared using a foam drying process as set forth below:

(1) preparation of a viscous liquid comprising an antigen, an adjuvant, and a polyol;

(2) formation of a mechanically stable porous structure ("foam") by boiling under a vacuum;

(3) exposure of the foam to a increased vacuum to eliminate water from the sample sufficient to increase the glass transition temperature of the mixture to a point above the desired storage temperature; and (4) cooling of the sample below the glass transition temperature to achieve a vitreous solid form of the antigen/adjuvant/polyol composition that has long-term stability at the storage temperature.

A feature of the vitreous compositions is that both antigens and adjuvants of the compositions retain their integrity (i.e., they do not significantly degrade or aggregate). For example, antigens in a vitreous composition are found to lack significant degradation. The integrity of the antigens is substantially maintained even when the vitreous compositions containing the antigens are stored over a period of time. In one example, protein antigens in a foam dried preparation lack substantial degradation and retain purity after storage at 25, 37 or 55° C. for 52 weeks. The integrity of adjuvants is also maintained in the vitreous compositions. In one example, aluminum salt adjuvants that have been foam dried do not aggregate or degrade as measured by light scattering and as observed by transmission electron microscopy.

A feature of the vitreous compositions is adsorption of the antigens to the adjuvants. Adsorption of antigens to adjuvants may also be referred to herein as binding of antigens to adjuvants, or association between antigen and adjuvant. A feature of the glasses and foamed preparations is that, generally, more antigen is adsorbed to adjuvant in those preparations as compared to liquid preparations of antigen and adjuvant that have not undergone the vitrification process. In one example, adsorption of antigen to adjuvant in the foam dried preparations is measured after the foam dried preparations are reconstituted into a liquid form. In one example, the adjuvants in these reconstituted preparations can be sedimented by centrifugation and separated from the liquid. The amount of antigen associated with or adsorbed to the adjuvant can then be determined. In one example, at least 10% of the antigen in a vitreous composition is adsorbed to the adjuvant. In one example, at least 20% of the antigen in a vitreous composition is adsorbed to the adjuvant. In one example, at least 30% of the antigen in a vitreous composition is adsorbed to adjuvant. In other examples, at least 40%, 50%, 60%, 70%, 80%, 90% or even 100% of the antigens in a vitreous composition is adsorbed to the adjuvants in the composition. This association between antigen and adjuvant is maintained when the vitreous compositions are stored at various temperatures for periods of weeks, months, or even years. In one example, antigen is shown to be adsorbed to adjuvant after the vitreous compositions are stored at 25, 37 or 55° C. for 52 weeks. Other storage temperatures may be used.

Formulations and Administration

The antigens in the solid vitreous compositions, and in the reconstituted liquid formulations of the vitreous compositions, retain their immunogenic activity or their ability to stimulate an immune response in an individual or mammal to which the composition is administered. Likewise, the adjuvants in the solid vitreous compositions, and in the reconstituted liquid forms of the vitreous compositions, retain their ability to enhance the immunogenicity of the antigens of the compositions.

In one example, the vitreous solid form of the antigen/adjuvant/polyol composition may be useful in the preparation of a vaccine. Generally, the vaccine is a pharmaceutically acceptable formulation of the antigen/adjuvant/polyol vitreous composition. In addition to the antigen, adjuvant and polyol components, the vaccine compositions may include one or more excipients that may include stabilizers, emulsifiers, preservatives, carriers as well as substances that affect pH and/or isotonicity. Other substances, including other therapeutic agents, may be included. These substances may be part of the vitreous composition or may be added to a reconstituted liquid formulation of the vitreous composition. These substances may perform a variety of functions, including enhancing stability, improving pharmaceutical acceptability, delivery and others.

Pharmaceutically acceptable formulation of the vaccine compositions may also include diluents and other excipients. Examples of diluents may include binder, disintegrants, or dispersants such as starch, cellulose derivatives, phenol, polyethylene glycol, propylene glycol or glycerin. Additional excipients may include polysorbate (Tween) 80 and others.

The vitreous solid form of the antigen/adjuvant/polyol composition may be presented in a kit form comprising the vitreous solid form of the antigen/adjuvant/polyol composition and a reconstitution solution comprising one or more pharmaceutically acceptable diluents to facilitate reconstitution of the vitreous solid for administration to a mammal using conventional or other devices. Such a kit would optionally include the device for administration of the liquid form of the composition (e.g. hypodermic syringe, microneedle array) and/or instructions for use.

The present disclosure also provides methods of eliciting an immune response in a mammal by administering the vitreous vaccine compositions, or formulations thereof, to individuals or other mammals. This may be achieved by the administration of a pharmaceutically acceptable formulation of the compositions to the mammal to effect exposure of the antigen/adjuvant to the immune system of the mammal. The administrations may occur once or may occur multiple times. In one example, the one or more administrations may occur as part of a so-called “prime-boost” protocol. Other administration systems may include time-release, delayed release or sustained release delivery systems.

Acceptable routes of administration include intradermal administration (by syringe or microneedle array systems), oral administration, rectal administration, topical administration, nasal administration, mucosal administration, intramuscular, intravenous, subcutaneous, or other parenteral routes of administration. Exposure of the mammal to the compositions disclosed herein may result in establishment of a temporary or permanent immune response in the mammal. The immune response may protect the mammal from subsequent exposure to the antigen, often by subsequent exposure to an infectious agent from which the antigen was derived. Therapeutic effects may also be possible.

The compositions and vaccines disclosed herein may also be incorporated into various delivery systems. In one example, the compositions may be applied to a “microneedle array” or “microneedle patch” delivery system for administration. These microneedle arrays or patches generally comprise a plurality of needle-like projections attached to a backing material and coated with a dried form of a vaccine. When applied to the skin of a mammal, the needle-like projections pierce the skin and achieve delivery of the vaccine, effecting immunization of the subject mammal.

In one embodiment, a solution comprising the antigen/adjuvant/polyol composition is applied to the microneedle array prior to the foam drying process and the coated microarray is then exposed to the foam drying process. In another embodiment, the viscous solution prepared in the initial step of the foam drying process (i.e., before the boiling process step) is coated onto the surface of a microneedle array and then the remainder of the foam drying procedure is applied to the viscous solution coated microneedle array. Under either procedure, a microneedle array coated with a vitreous composition comprising at least one antigen and at least one adjuvant results. Such arrays may be used to administer antigens, as well as antigens and adjuvants, to mammals to achieve an immune response to the antigen and vaccination of the mammal.

EXAMPLES

The following examples are for the purpose of illustrating an embodiment of the invention and are not to be construed as a limitation.

Example 1

Foam Drying of Antigen and Adjuvant

A mixture was prepared containing 3 mg of alum or aluminum phosphate adjuvant per ml, 200 μg of a protein antigen from *Streptococcus pneumoniae* termed PhtD (Adamou et al., Infect. Immun. 69:949-958, 2001) per ml, and 40% sucrose in sodium phosphate buffer (pH 7.2). The PhtD protein used in these studies had a predicted isoelectric point of 5.1. Control samples were prepared in accordance with the foregoing containing the PhtD protein and sucrose but devoid of aluminum adjuvant. This mixture was stored at 2-8° C. prior to drying to minimize the potential for protein degradation and to facilitate the association of antigen and adjuvant (e.g., 24-48 h). Alternatively, a phosphate buffered solution of the aluminum phosphate and PhtD protein were incubated alone, and sucrose was added later, before the drying process. Portions of the mixture were distributed into individual containers and dried at ambient temperature for 4 h under a low vacuum (hydrostatic pressure P=0.2 atm). The samples were then boiled for 4 h under a high vacuum (P<0.01 atm). During this latter step, a stable dry foam was formed in the individual containers. The samples were then stored for 8 days over DRIERITE (W. A. Hammond Drierite Co, Ltd. Xenia, Ohio 54385) under vacuum at 55° C. (secondary drying). These samples were then stored for various times, until resuspended to form an aqueous solution. The reconstituted samples were then used in various studies, as described in the Examples that follow.

Example 2

Effects of Foam Drying on Aluminum Adjuvant Stability

To evaluate the effects of foam drying on the integrity of aluminum adjuvants, reconstituted samples of foam dried material, prepared in substantial accordance with the disclosure in Example 1, were analyzed using a particle analyzer (Malvern Zetasizer), calibrated with respect to standards of known sizes, to determine the mean size of the particles contained within the samples. If the foam drying process were detrimentally affecting aluminum adjuvant integrity, this could be detected as a change in the mean particle size of the particles within the samples. For example, if foam drying caused degradation of the aluminum adjuvant, then particle sizes in the reconstituted samples would be smaller than those in an equivalent sample that had not been foam dried. In contrast, if foam drying caused aggregation of the aluminum adjuvant, then particle sizes in the reconstituted samples would be larger than those in an equivalent sample that had not been foam dried.

In FIG. 1 of the attached drawings, the particle sizes in reconstituted foam dried samples containing PhtD protein and sucrose (B) or containing PhtD protein, Alum and sucrose (C) were compared with liquid samples that had not been subjected to foam drying. The liquid samples that had not been foam dried included Alum alone (A), PhtD protein, Alum and sucrose (D), and PhtD protein and Alum (E). As illustrated, the mean particle size shown for the non-foam dried Alum (A) was indicative of the particle size for Alum that is neither degraded nor aggregated. The mean particle sizes, for non-foam dried samples containing PhtD protein, Alum and sucrose (D), and PhtD protein and Alum (E) were similar to those for the non-foam dried Alum alone (A). The mean particle size for the reconstituted foam dried sample containing PhtD protein, Alum and sucrose (C) were also similar to those of non-foam dried samples (A), (D) and (E). These data indicated that loam drying did not result in significant degradation or aggregation of aluminum adjuvants. The mean particle size of the reconstituted foam dried sample containing PhtD protein and sucrose (B) did appear smaller than the other samples tested.

Example 3

Effects of Foam Drying on Aluminum Adjuvant Stability

In an additional study relating to adjuvant stability, aluminum phosphate or aluminum hydroxide adjuvants, PhtD protein and 40% sucrose were prepared in substantial accordance with the disclosure in Example 1. The foam dried samples were reconstituted and analyzed using a particle analyzer (Malvern Mastersizer 2000), calibrated with respect to standards of known sizes, to determine the mean size of the particles contained within the samples.

Figure 2:
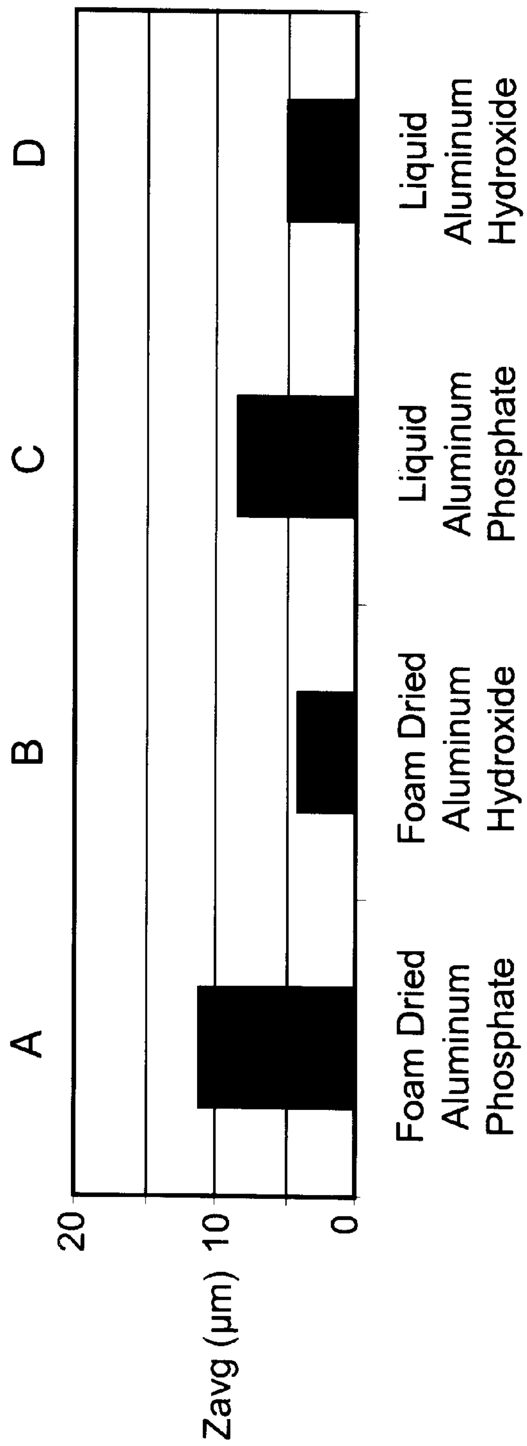
FIG. 2 illustrates example results of a study examining the effects of foam drying on aluminum adjuvant stability in various preparations as described in more detail in Example 3 herein. The vertical axis is a measure of mean particle size in microns.

In FIG. 2 of the attached drawings, the mean particle sizes in reconstituted foam dried samples containing aluminum phosphate adjuvant (A) or containing aluminum hydroxide adjuvant (B), were compared with liquid samples that had not been subjected to foam drying ((C) and (D), respectively). As illustrated, the mean particle size shown for the foam dried aluminum phosphate (A) was similar to that for the liquid aluminum phosphate (C). Similarly, the mean particle size shown for the foam dried aluminum hydroxide (B) was similar to that for the liquid aluminum hydroxide (D). These data indicated that foam drying did not result in significant degradation or aggregation of aluminum adjuvants.

Example 4

Appearance of Reconstituted Foam Dried Adjuvant Preparations by Transmission Electron Microscopy (TEM)

To evaluate the effects of foam drying on the integrity of aluminum adjuvants, reconstituted samples of foam dried material, prepared in substantial accordance with the disclosure in Example 1 (except that PhtD protein was omitted), were reconstituted and then prepared for transmission electron microscopy (TEM). Liquid samples, that had not been foam dried, were also prepared for TEM. As a control, aluminum adjuvants that were directly prepared for TEM (no sucrose) were also used. Electron micrographs were taken at direct magnifications from ×100,000 to ×150,000.

Figure 3:
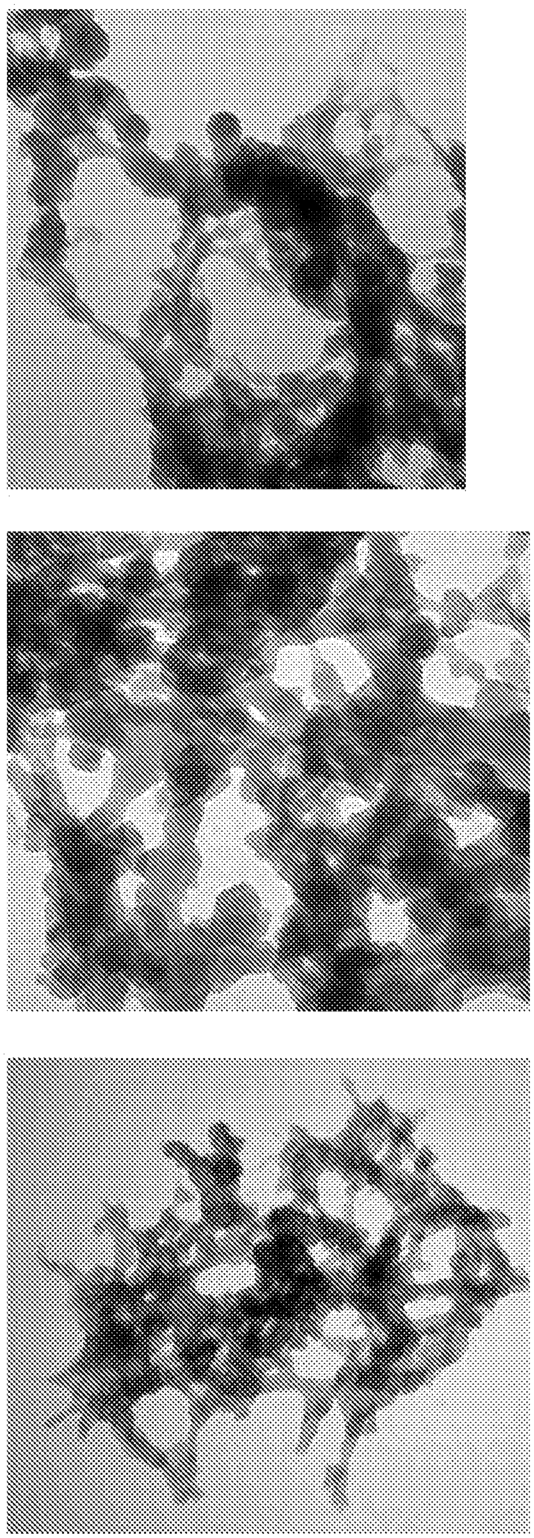
FIG. 3 illustrates example results of a study examining the appearance of reconstituted foam dried samples containing aluminum phosphate adjuvant by transmission electron microscopy as described in more detail in Example 4 herein. The electron micrographs in panels (A) and (B) were directly magnified 150,000 times. The electron micrograph in panel (C) was directly magnified 100,000 times.
Figure 4:
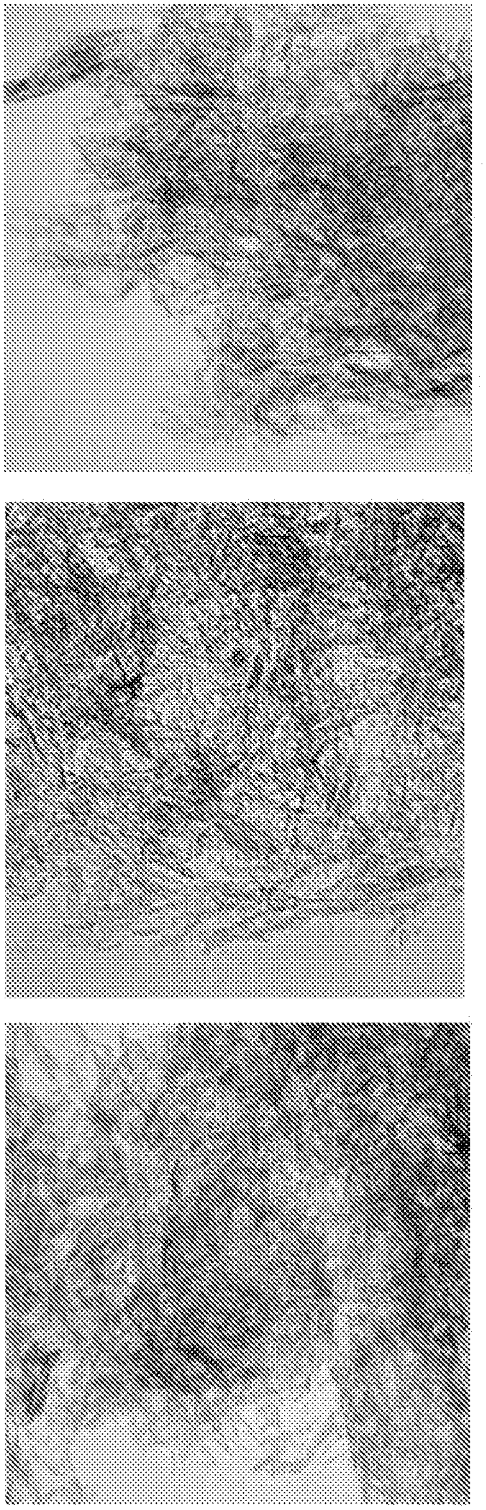
FIG. 4 illustrates example results of a study examining the appearance of reconstituted foam dried samples containing aluminum hydroxide adjuvant by transmission electron microscopy as described in more detail in Example 4 herein. The electron micrographs were directly magnified 100,000 times.

In FIG. 3 of the attached drawings, foam dried aluminum phosphate adjuvant (A), aluminum phosphate adjuvant that had not been foam dried (B), and aluminum phosphate adjuvant directly prepared for TEM (C) are shown. In FIG. 4 of the attached drawings, foam dried aluminum hydroxide adjuvant (A), aluminum hydroxide adjuvant that had not been foam dried (B), and aluminum hydroxide adjuvant directly prepared for TEM (C) are shown. These data indicated that foam drying did not result in significant aggregation of aluminum adjuvants.

Example 5

Effects of Polyol Concentration on Aluminum Adjuvant Stability During Foam Drying To evaluate the effects of different concentrations of polyols on the integrity of aluminum adjuvants during foam drying, foam dried aluminum phosphate adjuvant (3 mg/ml), PhtD protein (200 μg), and sucrose at a concentration of 40%, 30% or 5% were foam dried in substantial accordance with the disclosure in Example 1. The samples were then reconstituted and analyzed using a particle analyzer (Malvern Mastersizer 2000), calibrated with respect to standards of known sizes, to determine the mean size of the particles contained within the samples.

Figure 5:
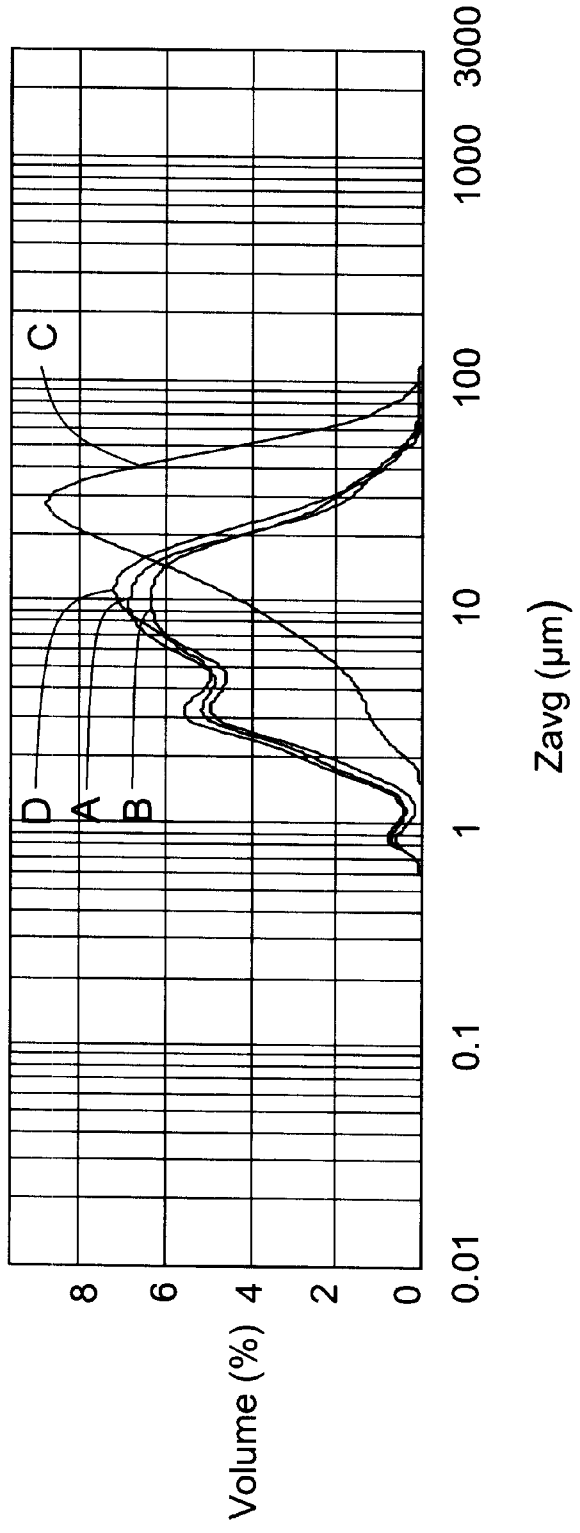
FIG. 5 illustrates example results of a study examining the effects of foam drying on aluminum adjuvant stability in preparations containing different concentrations of sucrose, as described in more detail in Example 5 herein. The vertical axis is a measure of percent of total volume. The horizontal axis is a measure of mean particle size in microns.

In FIG. 5 of the attached drawings, the particle sizes in the reconstituted foam dried samples that contained sucrose at 40% (A), 30% (B), and 5% (C) were compared with a liquid sample containing aluminum phosphate adjuvant, PhtD protein and 5% sucrose that had not been foam dried (D). As illustrated, the mean particle sizes of the aluminum adjuvant that had been foam dried in the presence of 40% sucrose (A) and 30% sucrose (B) were similar in size to one another, as well as to the 5% sucrose sample (D) that had not been foam dried. The sample sizes of these samples were similar to those illustrated in FIGS. 1 and 2. The mean particle size of the reconstituted sample that had been foam dried in the presence of 5% sucrose (D) was larger than that of the other samples. This may indicate that, at lower concentrations of the polyols (in this example, sucrose), that some aggregation of the aluminum adjuvant (in this example, aluminum phosphate adjuvant) may occur.

Example 6

Effects of Foam Drying on the Association Between Antigen and Aluminum Adjuvant

To evaluate the association between antigen and adjuvant, or adsorption of protein antigen to aluminum adjuvant, due to the foam drying process, the study described below was performed. This study examined the ability of foam drying to preserve, in a dry form, the associations formed between antigen and adjuvant formed in liquid and the extent to which the association between antigen and adjuvant in the dried foam was maintained when the dried sample was reconstituted.

In this study, PhtD protein and aluminum phosphate adjuvant, in 40% sucrose, were foam dried in substantial accordance with the disclosure in Example 1. The dried samples were then reconstituted in solution. As a control, an identical solution of PhtD protein, aluminum adjuvant and 40% sucrose, that was not foam dried, was incubated at 2-8° C. with rotation for 3.5 h. Both the foam dried and non-foam dried samples were then centrifuged to pellet the aluminum adjuvant contained in the sample, along with any protein adjuvant that was bound or adsorbed to the adjuvant. The supernatant from the centrifugation was analyzed for protein content using the Micro BCA Protein Assay Kit (Product No. 23235; Thermo Fisher Scientific; Rockford, Ill., USA) to determine, through comparison to standards, the amount of protein present in the supernatant. The protein in the supernatant was protein that had not bound to the aluminum adjuvant, and was free in solution. Because the amount of total protein in the foam dried samples was known (200 μg/ml; see Example 1), subtraction of the amount of protein unbound to adjuvant (as determined by the colorimetric reaction used to assay protein in the supernatant) from the amount of total protein in the samples, yielded the amount of protein adsorbed to the adjuvant.

Figure 6:
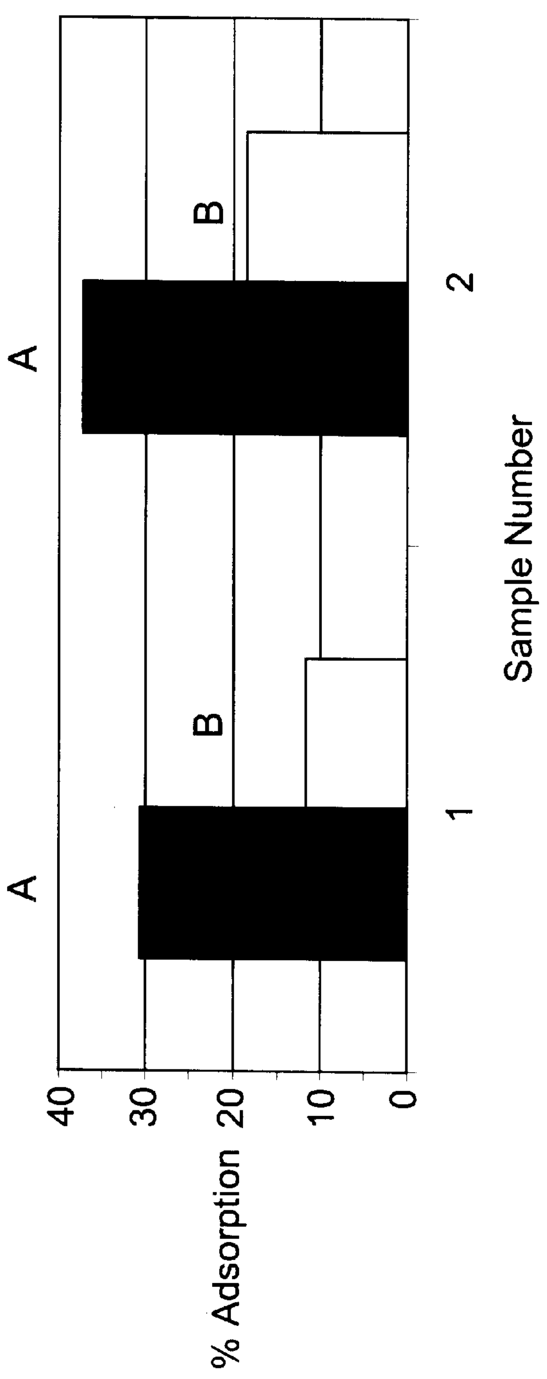
FIG. 6 illustrates example results of a study examining the effects of foam drying on adsorption of a protein antigen to an aluminum adjuvant, as described in more detail in Example 6 herein. Percent of protein antigen that was adsorbed to the adjuvant is shown on the y-axis. The experiment was done in duplicate (indicated as sample number 1 and 2 on the x-axis).

The results of the study are presented in FIG. 6 of the attached drawings. Percent of protein antigen that was bound to adjuvant is shown on the y-axis. The experiment was performed in duplicate and sample numbers 1 and 2 are indicated on the x-axis. The data showed that, in the foam dried samples (A), there was more adsorption of the protein adjuvant to the aluminum phosphate adjuvant (between about 30-40% in this study) than in the non-foam dried samples (B; between about 10-20% in this study). These data indicated that foam drying enhanced the association or adsorption of antigen and adjuvant formed in solution. These data also indicated that the association between antigen and adjuvant in the dried preparation was maintained when the sample was reconstituted.

Example 7

Foam Drying Effects on Association Between Antigen and Aluminum Adjuvant Over Time To evaluate the association between antigen and adjuvant due to foam drying, over time, the following studies were performed. In the first study, PhtD protein and aluminum adjuvant were foam dried in substantial accordance with the disclosure in Example 1. The foam dried samples were stored at 25° C. for a period of from 0 to 52 weeks and were then reconstituted. Approximately 24 h before the foam dried samples were reconstituted, non-foam dried liquid samples (PhtD protein, aluminum phosphate adjuvant, 40% sucrose) were prepared in phosphate-buffered saline (PBS), pH 7.2, and incubated at 2-8° C. for 24 h. These latter samples were used as controls for non-foam dried preparations. For each time point, both the foam dried and non-foam dried samples were centrifuged to pellet the aluminum adjuvant contained in the sample, along with any protein adjuvant that was bound to the adjuvant. The supernatant from the centrifugation was analyzed by reverse phase high performance liquid chromatography (RP-HPLC) to determine, through comparison to standards, the amount of protein present in the supernatant. As in Example 6, the amount of protein in the supernatant was used to calculate the amount of protein adsorbed to the adjuvant.

Figure 7:
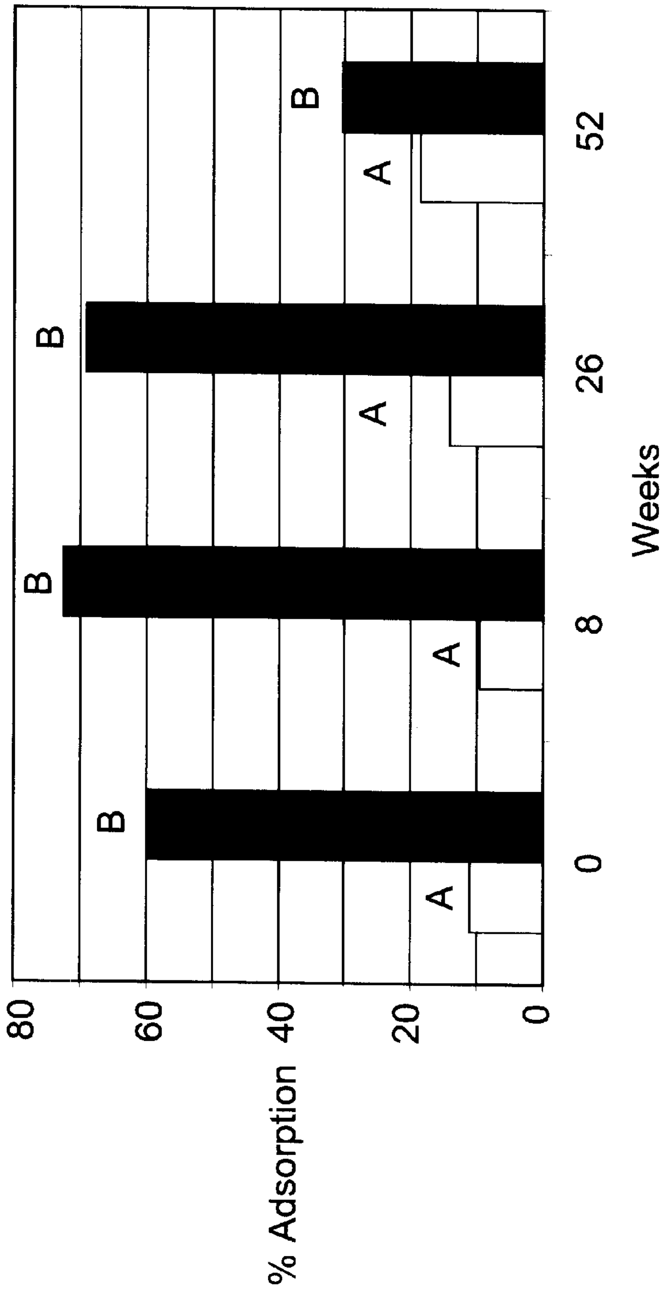
FIG. 7 illustrates example results of a study examining adsorption of a protein antigen to an aluminum adjuvant in a foam dried preparation over time, as described in more detail in Example 7 herein. Percent of protein antigen that was adsorbed to the adjuvant is shown on the y-axis. On the x-axis, the time in weeks at which the various samples were analyzed is shown.

The results of the study are presented in FIG. 7 of the attached drawings. Percent of protein antigen that was adsorbed to adjuvant is shown on the y-axis. On the x-axis, the time in weeks that the foam dried samples were stored at 25° C. is indicated. The foam dried samples are indicated as (B). The non-foam dried samples are indicated as (A). At 0 weeks, in this example study, approximately 60% of the protein antigen was found to be adsorbed to the aluminum adjuvant in the foam dried sample. This compares with approximately 10% of the protein antigen adsorbed to the aluminum adjuvant in the non-foam dried, liquid control sample. In this study, the amount of protein antigen adsorbed to the aluminum adjuvant was found to be approximately 70% at both 8 and 26 weeks in the foam dried samples, while the amount of protein antigen adsorbed to aluminum adjuvant in the non-foam dried, liquid samples remained below 20% at both time points. In this study, the amount of protein antigen adsorbed to aluminum adjuvant was found to have decreased at 52 weeks in the foam dried sample, but was still higher than the non-foam dried, liquid control at this time point. These data indicated that the association between antigen and adjuvant was stable over time in foam dried preparations stored at 25° C.

Example 8

Effect of Storage Temperature on the Association Between Antigen and Aluminum Adjuvant in Foam Dried Preparations Over Time To evaluate the association between antigen and adjuvant in foam dried samples over time when the samples were stored at different temperatures, the following study was performed. Preparations of antigen and adjuvant in sucrose were foam dried in substantial accordance with the teaching of Example 1. The dried samples were then stored, at either 25° C. or 37° C., for a period of 8 or 12 weeks. At the end of the storage period, the dried samples were reconstituted in an aqueous solution. The samples were then centrifuged to pellet the aluminum adjuvant contained in the sample, along with any protein adjuvant that was adsorbed to the adjuvant. The supernatant from the centrifugation was analyzed by RP-HPLC, to determine the amount of protein present in the supernatant, and the amount of protein adsorbed to the adjuvant, as described in Example 7. At each time point, the amount of protein adsorbed to adjuvant in foam dried samples was compared to the amount of protein adsorbed to adjuvant in non-foam dried, liquid samples as a control.

Figure 8:
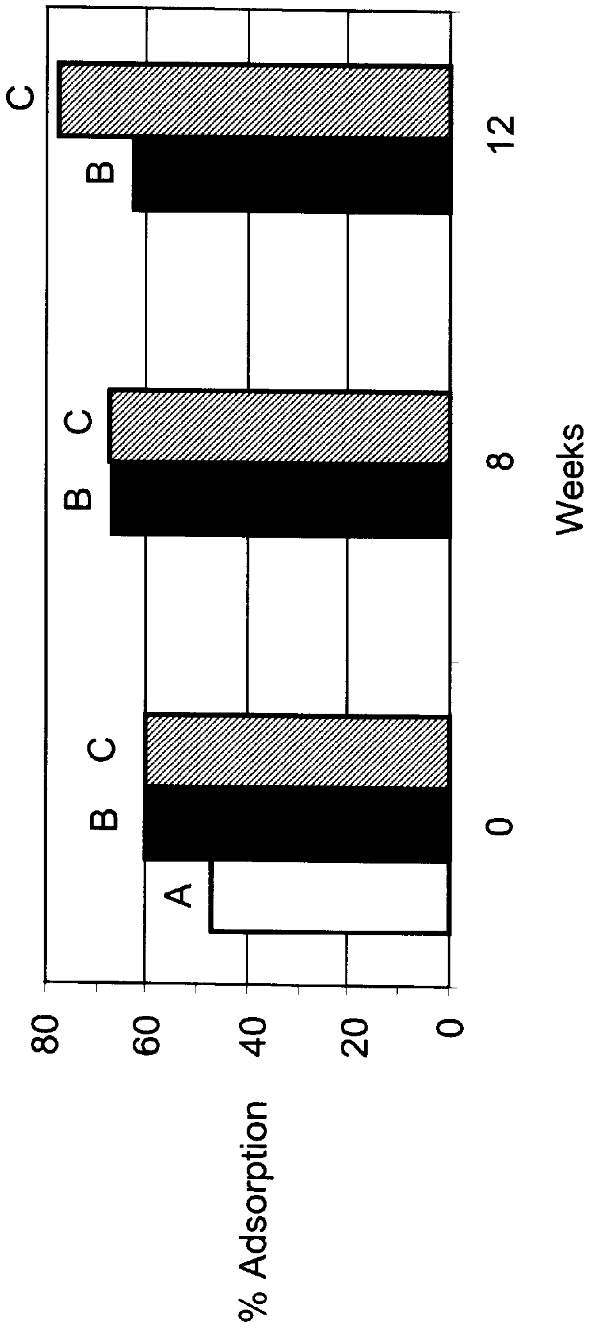
FIG. 8 illustrates example results of a study examining adsorption of a protein antigen to an aluminum adjuvant in a foam dried preparation over time, as described in more detail in Example 8 herein. Percent of protein antigen that was adsorbed to the adjuvant is shown on the y-axis. On the x-axis, the time in weeks at which the various samples were analyzed is shown.

The results of the study are presented in FIG. 8 of the attached drawings. Percent of protein antigen that was bound to adjuvant is shown on the y-axis. On the x-axis, the time in weeks in which the foam dried samples were stored before analysis is indicated. At 0 weeks, sample (A) shows the amount of protein bound to adjuvant in a liquid sample containing protein and adjuvant in phosphate buffer at 2-8° C. that was not foam dried to be between 40-50%. Samples (B) and (C) at 0 weeks show the amount of protein adsorbed to adjuvant in foam dried samples that had been stored for a minimal period of time at 25° C. (B) or 37° C. (C) and then were reconstituted in aqueous solution. These data showed the percent of protein adsorbed to adjuvant was approximately 60% in both the (B) and (C) samples. When the foam dried samples were stored for 8 weeks before reconstitution, the amount of protein adsorption to adjuvant, at both 25° C. (B) and 37° C. (C), was similar to those found in the samples analyzed at 0 weeks. Likewise, when the foam dried samples were stored for 12 weeks before reconstitution and analysis, the amount of antigen adsorbed to adjuvant, at both 25° C. (B) and 37° C. (C), were similar to, and possibly even greater than, the amounts of antigen adsorbed to adjuvant at both 0 and 8 weeks. These data indicated that the association between the protein antigen and adjuvant was stable over time in the foam dried preparation at both 25 and 37° C.

Example 9

Effects of Different Stabilizing Agents, Secondary Drying Temperatures, and Different Storage Temperatures on Protein Antigen in Foam Dried Preparations To evaluate a number of factors (e.g., stabilizers, secondary drying temperatures, storage temperature of foam dried preparations) on the stability of protein adjuvants in foam dried preparations, the following study was performed. Mixtures were prepared as shown in Table 1 below and were then foam dried in substantial accordance with the disclosure in Example 1. After the boiling step to form the foam, secondary drying was performed on some samples at 40° C. and on other samples at 55° C.

TABLE 1

Formulations for Foam Drying

| Formulation | Mixture composition (100 ml)[1] Stabilizers | Adjuvant |
|---|---|---|
| F1 | 40 g sucrose | 300 mg aluminum phosphate |
| F2 | 40 g sucrose<br>5 g arginine<br>5 g monosodium glutamate | None |
| F3 | 20 g sucrose<br>20 g methyl α-D-glucoside | None |
| F4 | 40 g 2-HP-β-cyclodextrin<br>5 g arginine<br>5 g monosodium glutamate | None |
| F5[2] | 40 g sucrose | 600 mg aluminum phosphate |
| F6 | 13.2 g 2-HP-β-cyclodextrin<br>4.98 g arginine<br>1.65 g monosodium glutamate<br>13.3 g sucrose | None |

[1]All mixtures were prepared in 10 mM sodium phosphate buffer (pH 7.0) and contained 200 μg PhtD protein per ml.
[2]Prepared by incubating PhtD protein and aluminum phosphate adjuvant at 2-8° C. for 24 h before adding polyol.

Figure 9:
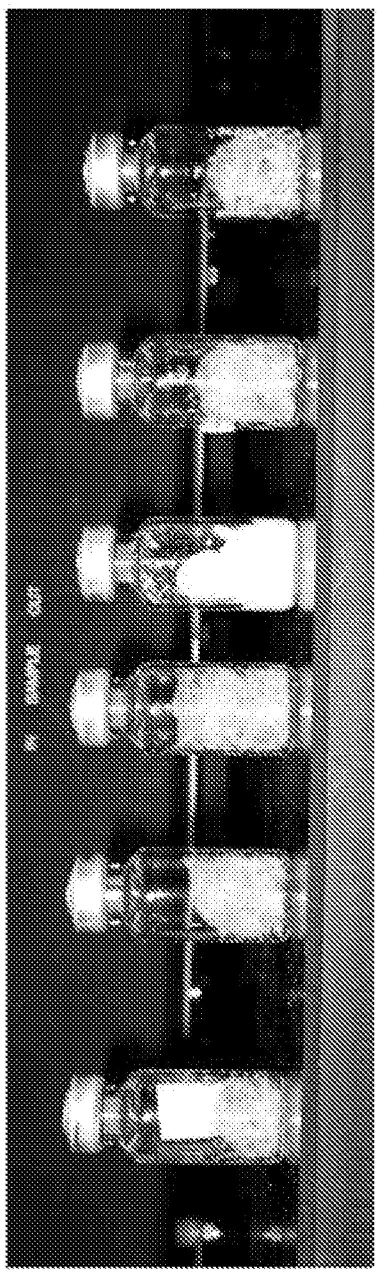
FIG. 9 illustrates example vials of foam dried formulations produced as described in Example 9 herein.

After completion of the secondary drying step, the appearance of the samples was noted (FIG. 9 of the attached drawings). The samples generally appeared as foams (F1, F2, F3, F5 and F6). One sample (F4) appeared as a dense cake.

Also after completion of the secondary drying step, the residual moisture content of the samples was determined using the Karl Fisher volumetric titration technique (see U.S. Pat. No. 4,740,471). This technique measures percentage of water by weight relative to the total weight of the dried product. These data are shown in Table 2 below.

TABLE 2

Residual Moisture Content of Foam Dried Formulations

| Formulation | Residual moisture (% by weight) after secondary drying at specific temperature 40° C. | 55° C. |
|---|---|---|
| F1 | 2.75 | 1.05 |
| F2 | 3.67 | 1.79 |
| F3 | 0.58 | 0.21 |
| F4 | 0.41 | 0.18 |
| F5 | 3.06 | 1.44 |
| F6 | 2.28 | 1.21 |

The results showed that the residual moisture content in the samples where secondary drying was performed at 55° C. was generally less than in the samples where secondary drying was performed at 40° C.

The foam dried samples were then stored at either 23-27° C. (indicated as 25° C.), 35-39° C. (indicated as 37° C.), or 53-57° C. (indicated as 55° C.) over a period of 12 months. During this time period, the appearance of the samples stored at 25 and 37° C. did not appear to change substantially, except for some changes in coloration. However, for the samples stored at 55° C., the foams generally appeared "melted" after 12 months. The F6 sample, however, did still appear as a foam after storage at 55° C. for 12 months.

To determine stability of the protein antigen in the foam dried samples stored at the various temperatures during the 12 month storage period, the foam dried samples were reconstituted as aqueous solutions at various times and then analyzed by RP-HPLC. Percent purity of the protein antigen was calculated by determining the amount of protein present in the main protein peak obtained from the RP-HPLC column and dividing this value by the amount of protein present in all protein peaks obtained from the column. Percent purity is an indicator of stability of the protein over time.

The results showed that generally, for all tested formulations, for secondary drying at both 40 and 55° C., purity of the protein generally remained above 80 to 90% over the 12 month storage period, for all temperatures at which the samples were stored (i.e., 25, 37 and 55° C.).

Total recovery of input protein from the RP-HPLC column was generally around 80% in this study. However, in some instances, recovery appeared to be lower. Recovery of protein from the adjuvant-containing F1 and F5 formulations, in which secondary drying had been performed at 40° C., and which had been stored at 55° C., were found to be below 20% after 1 week. Also, recovery of protein from the F1 formulation in which secondary drying had been performed at 55° C., and had been stored at all tested temperatures (i.e., 25, 37 and 55° C.) was approximately 60-65%.

Example 10

Formation and Quality of Foam Dried Preparations Using Different Aluminum Adjuvants To evaluate the formation and quality of foam dried preparations using different aluminum adjuvants (i.e., aluminum phosphate adjuvant and aluminum hydroxide adjuvant), the following study was performed. Mixtures were prepared as shown in Table 3 below and were then foam dried in substantial accordance with the disclosure in Example 1. Secondary drying was performed at 55° C.

TABLE 3

Formulations for Foam Drying

| Formulation | Mixture composition (100 ml)[1] Adjuvant | Buffer |
|---|---|---|
| F6 | 300 mg aluminum phosphate | 10 mM sodium phosphate |
| F7 | None | 10 mM sodium phosphate |
| F8 | 125 mg aluminum oxyhydroxide | 10 mM Tris-HCl |
| F9 | None | 10 mM Tris-HCl |
| F10 | 300 mg aluminum phosphate | Phosphate buffered saline |

[1]All mixtures contained 40 g sucrose and 200 μg PhtD protein per ml. All mixtures were prepared by gentle mixing of PhtD protein ± adjuvant at 2-8° C. for 24 h before adding sucrose.

After formation of the foam dried preparations, the residual moisture content of the samples was determined using the Karl Fisher volumetric titration technique. These data are shown in Table 4 below.

TABLE 4

| Residual Moisture Content of Foam Dried Formulations | |
|---|---|
| Formulation | Residual moisture (% by weight) after secondary drying at 55° C. |
| F6 | 1.38 |
| F7 | 1.60 |
| F8 | 1.40 |
| F9 | 1.22 |
| F10 | 1.61 |

The foam dried samples were then stored at either 23-27° C. (indicated as 25° C.) or 35-39° C. (indicated as 37° C.) over a period of 12 months. No substantial differences in appearance of the samples was observed during this period. Percent purity of the protein antigen, determined as described in Example 9, remained above 95% for the formulations stored at 25° C., and generally above 90% for the formulations stored at 37° C., for the 12 month period. Total recovery of input protein, also determined as described in Example 9, generally remained consistent for a given formulation during for the 12 month period.

To evaluate adsorption of the protein antigen to the aluminum adjuvants over time, the foam dried formulations were reconstituted in solution and the percentage of protein adsorbed to the aluminum adjuvant was determined as described in Example 7.

Figure 10:
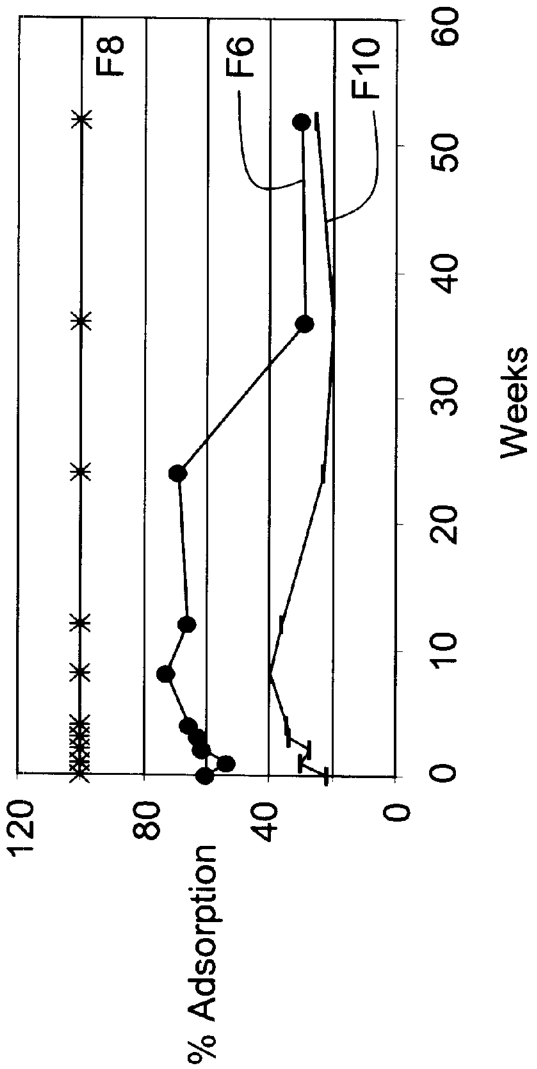
FIG. 10 illustrates example results of a study examining adsorption of a protein antigen to different adjuvants over time in dried foams where secondary drying was performed at 25° C., as described in more detail in Example 10 herein. Percent of protein adjuvant that was adsorbed to the adjuvant is shown on the y-axis. On the x-axis, the time in weeks at which the various samples were analyzed is shown.
Figure 11:
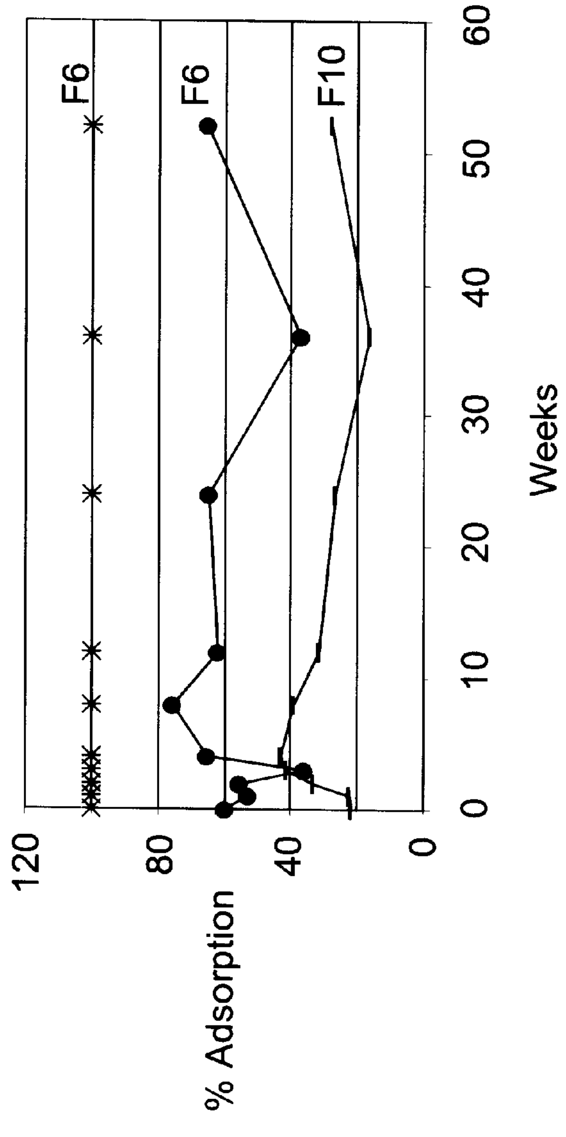
FIG. 11 illustrates examples results of a study examining adsorption of a protein antigen to different adjuvants over time in dried foams where secondary drying was performed at 37° C., as described in more detail in Example 10 herein. Percent of protein adjuvant that was adsorbed to the adjuvant is shown on the y-axis. On the x-axis, the time in weeks at which the various samples were analyzed is shown.

The results of the adsorption experiments are shown in FIG. 10, for storage of the foam dried formulations at 25° C., and in FIG. 11 for storage of the foam dried formulations at 37° C. In both figures, percent of protein adsorbed to adjuvant (y-axis) over time in weeks (x-axis) is shown for F8 (·X·), F6 (●) and F10 (■) as indicated in the figures. The data showed that adsorption of PhtD protein to aluminum hydroxide in Tris buffer (F8) was better than adsorption of PhtD protein to aluminum phosphate in sodium phosphate buffer (F6), which was better than adsorption of PhtD protein to aluminum phosphate in PBS (F10).

While example compositions, methods, and so on have been illustrated by description, it is not the intention of the applicants to restrict or in any way limit the scope of the application. It is, of course, not possible to describe every conceivable combination of components or methodologies for purposes of describing the compositions, methods, and so on described herein. Additional advantages and modifications will readily appear to those skilled in the art. Therefore, the invention is not limited to the specific details, the representative apparatus, and illustrative examples shown and described. Thus, this application is intended to embrace alterations, modifications, and variations that fall within the scope of the application. Furthermore, the preceding description is not meant to limit the scope of the invention. Rather, the scope of the invention is to be determined by the appended claims and their equivalents. To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use.

We claim:

1. A method for preparing a vitreous composition of an antigen and an adjuvant, comprising:

a) preparing a first liquid by incubating, storing, or mixing at least one antigen and at least one adjuvant at 2-8° C. for at least 24 hours;

b) subsequently adding at least one polyol or synthetic polymer to the first liquid to prepare a second liquid;

c) subsequently drying the second liquid at ambient temperature under low vacuum; and, d) subsequently boiling the product of c) under a high vacuum to form a foam.

2. The method of claim 1, wherein the foam substantially lacks crystalline structure.

3. The method of claim 1, wherein at least 30% of the antigen in the foam is adsorbed to the adjuvant.

4. The method of claim 3, wherein at least 50% of the antigen in the foam is adsorbed to the adjuvant.

5. The method of claim 4, wherein at least 60% of the antigen in the foam is adsorbed to the adjuvant.

6. The method of claim 1, wherein the polyol is present in the second liquid at the concentration of 30%.

7. The method of claim 1 wherein the polyol is sucrose.

8. The method of claim 1, wherein the at least one antigen and at least one adjuvant are mixed at 2-8° C. for 24 hours.

* * * * *